United States Patent

Schlichter et al.

[11] Patent Number: 6,087,608
[45] Date of Patent: Jul. 11, 2000

[54] METHOD AND APPARATUS FOR RECOGNIZING FOREIGN SUBSTANCES IN AND SEPARATING THEM FROM A PNEUMATICALLY CONVEYED FIBER STREAM

[75] Inventors: Stefan Schlichter, Viersen; Thomas Kramer, München, both of Germany

[73] Assignee: Trützschler GmbH & Co. KG, Mönchengladbach, Germany

[21] Appl. No.: 08/900,466

[22] Filed: Jul. 25, 1997

[30] Foreign Application Priority Data

Aug. 8, 1996 [DE] Germany .......................... 196 31 929
May 30, 1997 [DE] Germany .......................... 197 22 537

[51] Int. Cl.[7] .................................................. B07C 5/342
[52] U.S. Cl. ...................... 209/580; 209/587; 209/588; 209/938; 250/223 R; 250/226; 356/402
[58] Field of Search .................................. 209/577, 580, 209/581, 582, 587, 588, 656, 938, 939; 250/222.1, 223 R, 226; 356/402, 407

[56] References Cited

U.S. PATENT DOCUMENTS

| | | | |
|---|---|---|---|
| 5,135,114 | 8/1992 | Satake et al. | 209/581 X |
| 5,443,164 | 8/1995 | Walsh et al. | 209/587 X |
| 5,626,237 | 5/1997 | Hergeth | 356/402 X |
| 5,791,489 | 8/1998 | Leifeld | 209/567 X |

FOREIGN PATENT DOCUMENTS

| | | |
|---|---|---|
| 402543 | 12/1990 | European Pat. Off. ............... 209/588 |
| 0 414 961 | 3/1991 | European Pat. Off. . |
| 0 545 129 | 6/1993 | European Pat. Off. . |
| 195 05 421 | 8/1996 | Germany . |
| 2 029 590 | 8/1992 | Spain . |

*Primary Examiner*—Tuan N. Nguyen
*Attorney, Agent, or Firm*—Venable; Gabor J. Kelemen

[57] ABSTRACT

A fiber processing method includes the steps of removing fiber tufts from a series of fiber bales; pneumatically conveying the fiber tufts in a duct; forming images of the conveyed material as it passes through a first location of the duct; determining the degree of lightness or the color of the fiber tufts by an image processing device; determining the degree of lightness of foreign substances, conveyed with the fiber tufts, by the image processing device; comparing the measuring values obtained by the image processing device with a settable limit value; and initiating a switching operation when the limit value is exceeded for branching off to a waste receiver the fiber tufts from the duct at a second location thereof.

18 Claims, 5 Drawing Sheets

METHOD AND APPARATUS FOR RECOGNIZING FOREIGN SUBSTANCES IN AND SEPARATING THEM FROM A PNEUMATICALLY CONVEYED FIBER STREAM

CROSS REFERENCE TO RELATED APPLICATION

This application claims the priority of German Application Nos. 196 31 929.3 filed Aug. 8, 1996 and 197 22 537.3 filed May 30, 1997, which are incorporated herein by reference.

BACKGROUND OF THE INVENTION

This invention relates to a method and an apparatus in a spinning preparation (fiber cleaning) plant for recognizing foreign substances, such as fabric fragments, bands, strings, foil or other thin material and the like and separating them from a pneumatically conveyed fiber which has been removed by a bale opener from fiber bales. The apparatus includes an optical sensor device for recognizing foreign substances and a separating device arranged downstream of the optical sensor device, as viewed in the direction of fiber travel, for separating the foreign substances from the fiber stream. Further, the optical sensor device is connected with the separating device by means of an evaluating device (image processing unit) and a control device.

According to a known method foreign substance recognition is effected subsequent to a preliminary (coarse) cleaning or after a mixing step, that is, prior to a fine cleaning. The fiber tufts are admitted via a suction condenser to a delivery chute, one wall of which is formed by an endlessly circulating, obliquely oriented conveyor belt. Thereafter, the fiber tufts are moved by the belt to an optical recognition system. An evaluating device processes the measurements and if foreign substances are detected, the appropriate sectors of a nozzle bank are activated. The nozzles of a section are actuated as soon as the upstream arranged optical sensor device has recognized the foreign substances. The blast emanating from the nozzles blows the fiber tufts—with which the foreign substances are commingled—into a collecting bin. The other, non-contaminated good fibers are admitted into a collecting funnel and are advanced therefrom to a subsequent cleaning machine. It is a disadvantage of such a conventional arrangement that the conveying device requires a substantial technical and constructional outlay. It is a further drawback that the method permits only an actuation of the separating device for all the examined fibers tufts at the same time.

SUMMARY OF THE INVENTION

It is an object of the invention to provide an improved method and an apparatus of the above-outlined type from which the discussed disadvantages are eliminated and which, in particular, makes possible in a simple manner an improved recognition of foreign substances and a separation thereof from a pneumatically conveyed fiber stream.

This object and others to become apparent as the specification progresses, are accomplished by the invention, according to which, briefly stated, the fiber processing method includes the steps of removing fiber tufts from a series of fiber bales; pneumatically conveying the fiber tufts in a duct; forming images of the conveyed material as it passes through a first location of the duct; determining the degree of lightness or the color of the fiber tufts by an image processing device; determining the degree of lightness of foreign substances, conveyed with the fiber tufts, by the image processing device; comparing the measuring values obtained by the image processing device with a settable limit value; and initiating a switching operation when the limit value is exceeded for branching off to a waste receiver the fiber tufts from the duct at a second location thereof.

By virtue of the measures according to the invention, an improved setting of the sensitivity of the separating device may be obtained. In contrast to known processes, based on the evaluated measuring values (generated by the image processing device) relative to the lightness and/or color of the fiber material, the sensitivity of the separation may be individually set for bale groups or even for individual bales. As a result, for the bale groups or the individual fiber bale a lesser quantity of good fiber tufts is separated relative to the foreign substances and thus the degree of efficiency is significantly improved. The invention makes further possible a differentiated actuation of the separating device dependent upon the lightness characteristics of the fiber material and/or the foreign substances. The limit values for the actuation of the separating device are differently set in each instance.

The method according to the invention includes the following advantageous additional features:

- At least one test run is performed in which the lightness characteristics of the fiber material is determined.
- Based on the lightness and/or color characteristics of the fiber material, the limit value or, as the case may be, the limit range is determined in which no separation of foreign substances takes place.
- The detected measuring signals are evaluated in a signal analysis system.
- The analyzed characterizing signal magnitudes of the test run are stored in a memory and compared with the actual characterizing signal magnitudes of the test run.
- During the test runs a mean lightness value is formed.
- A mean value is formed for all fiber bales of a fiber bale series.
- A mean value is formed for each bale group (for example, having the same fiber type) of one bale series.
- The separating sensitivity is determined in defined boundaries for all types of fiber material.
- The separating sensitivity is determined at one distance relative to the lightness and/or color characteristic for a certain fiber material.
- The separating sensitivity is determined at a variable distance relative to the lightness and/or color characteristic of a fiber material dependent upon typical properties of the foreign substances.
- The location of each fiber bale within a fiber bale series is determined and is associated with the lightness and/or degree of soiling of the fiber material of the fiber bales or the fiber bale group from which the fiber material (fiber tufts) has been obtained.
- With each fiber bale a limit value is associated for the switching process of the separating device.
- The limit value is determined for each fiber bale based on the measuring values of the image processing device.

The invention further relates to an apparatus incorporated in a spinning preparation (cleaning) line for recognizing and separating foreign substances from fiber tufts removed from fiber bales. The apparatus has an optical sensor device for recognizing the foreign substances and a separating device which is arranged downstream of the sensor device as viewed in the direction of fiber advance and wherein the optical sensor device is connected with the separating device via an evaluating device and a control device and further, the optical device is connected to the image processing device which, in turn, is coupled to an electronic control and regulating device.

BRIEF DESCRIPTION OF THE DRAWINGS

FIG. 6b is a diagram, associated with FIG. 6a, showing characteristic material curves associated with respective bales shown in FIG. 6a.

FIG. 6c is a diagram showing separating sensitivities relating to the respective fiber bales illustrated in FIG. 6a.

DESCRIPTION OF THE PREFERRED EMBODIMENTS

Figure 1:
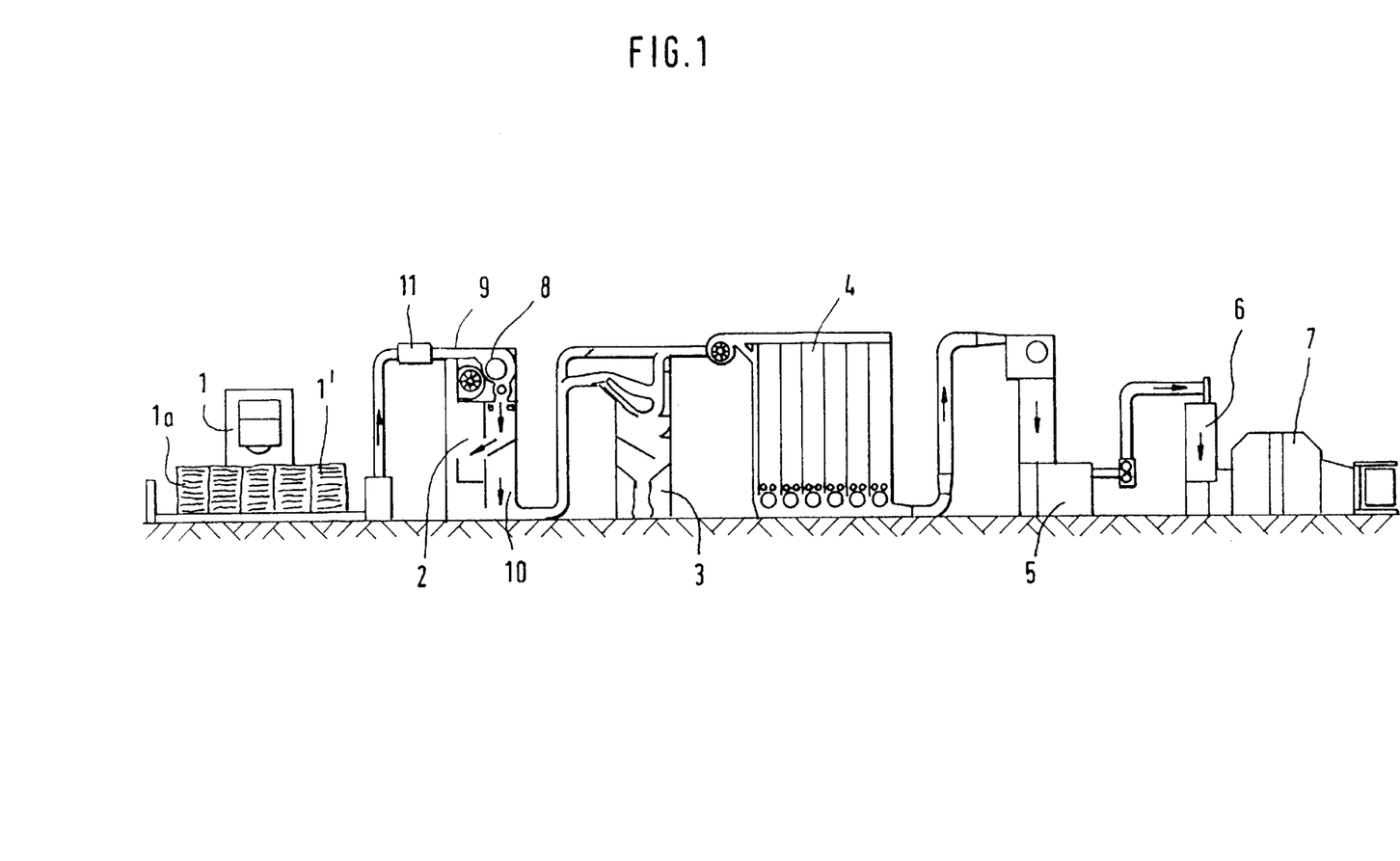
FIG. 1 is a schematic side elevational view of a fiber processing (opening, cleaning and carding) line incorporating the apparatus according to the invention.

FIG. 1 illustrates a cleaning line in which an apparatus 2 for recognizing and separating metal foreign substances and a heavy particle separator 3 are arranged between a bale opener 1 which may be, for example, a BLENDOMAT BDT model manufactured by Trützschler GmbH & Co. KG, Mönchengladbach, Germany and a multi-mixer 4. Downstream of the multi-mixer 4, as viewed in the direction of travel of the processed fiber a fine opener 5 is arranged which supplies fiber tufts to a plurality of card feeders 6 (only one shown) each associated with a carding machine 7 (only one shown). The bale opener 1 in which a series of fiber bales 1a stand, is coupled with a condenser 8 (including a screening drum) by means of a pneumatic conduit 9. Further, the chute 10 situated downstream of the condenser 8 and the other downstream-arranged machines are interconnected by means of pneumatic conduits. The inventive apparatus 11 is positioned in the conduit 9, that is, it is arranged immediately downstream of the bale opener 1.

Figure 2:
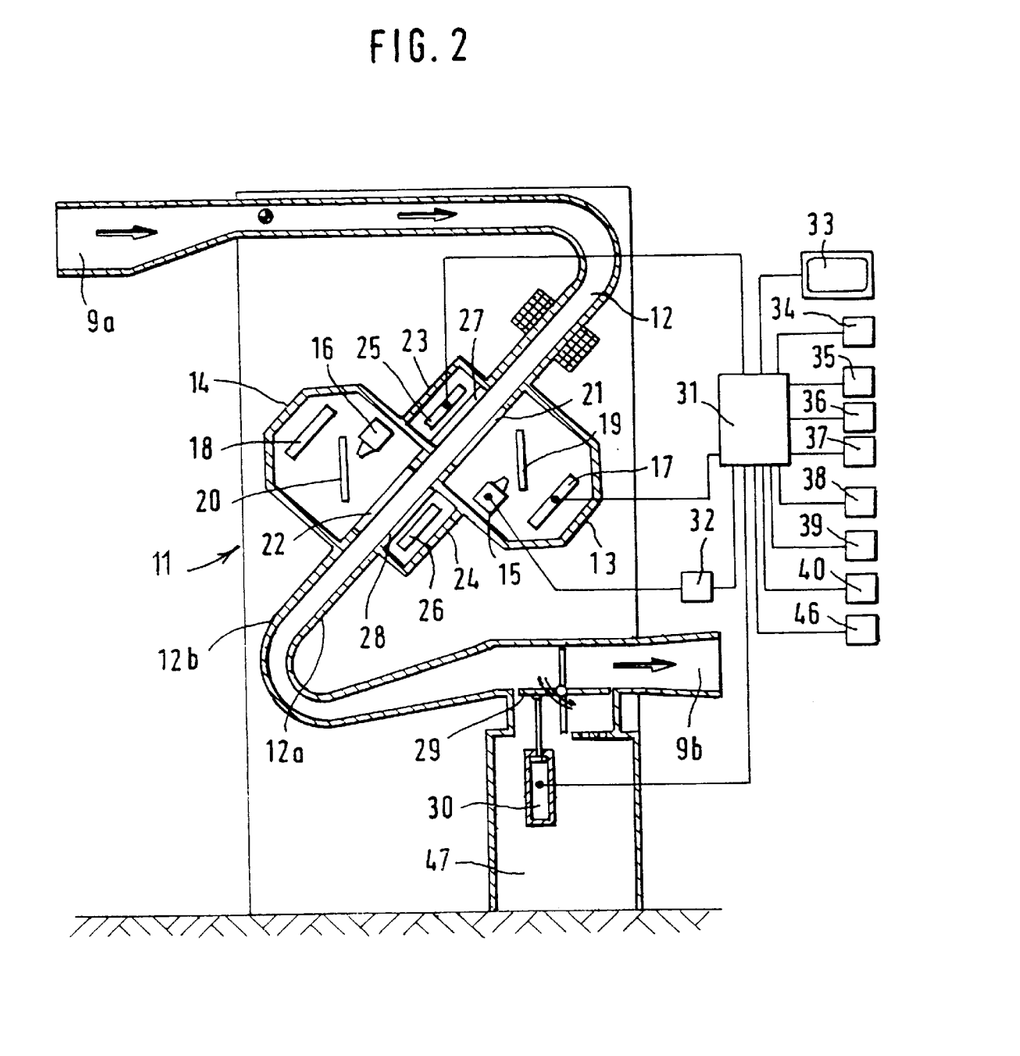
FIG. 2 is a schematic sectional side elevational view of the apparatus according to the invention, including an optical sensor device having two cameras and four illuminating devices for picture taking in transmitted and reflected light, an image processing device and an electronic control and regulating device.

Turning to FIG. 2, there are illustrated details of the apparatus 11. The inlet of a throughgoing duct 12 is coupled to a portion 9a of the conduit 9 whereas the outlet of the duct 12 is coupled to a portion 9b of the conduit 9.

To the outside of the duct 12 two housings 13 and 14 are mounted in which respective cameras 15 and 16 as well as illuminating devices 17 and 18 are disposed. Further, in the housings 13 and 14 respective deflecting mirrors 19 and 20 are arranged which deflect the optical axis between the cameras 15 and 16 and respective windows 21 and 22 provided in the wall of the duct 12 and situated within the outline of the respective housings 13 and 14. The illuminating devices 17 and 18 send light through the windows 21 and 22 into the inner space of the duct 12. On the side opposite the housings 13 and 14 two further housings 23 and 24 are mounted on the outside of the duct 12. In the housings 23 and 24 respective illuminating devices 25 and 26 are disposed which send light through duct windows 27 and 28 into the space of the duct 12. The housings 13, 23 and the housings 14, 24 are arranged offset with respect to one another as viewed in the direction of material flow through the duct 12.

The apparatus (fiber tuft sensor) according to the invention makes possible a recognition of foreign substances in a pneumatically conveyed stream of cotton tufts. Particularly the following types of substances (foreign bodies) are detected:

Non-transparent substances such as wood, stones, metal, strings, paper, etc; substances which are set off by their color from the fiber tufts, such as soil, leaves, etc. and bright components such as film or foil parts.

For performing the measuring process the cotton tufts are conveyed through the cross-sectionally rectangular duct 12. As the tufts fly by the windows 21, 27; 22, 28 provided in the duct walls 12a, 12b, they are detected by the cameras 15 and 16. The detecting process includes the utilization of reflected light and transmitted light by mean of flash illumination by the illuminating devices 17, 25; 18, 26. The evaluation is performed according to the principle of actual and desired value comparison. As a desired parameter, the reflected beam intensity related to the transmitted beam intensity is utilized. The characteristic (lightness and color) of the cotton is automatically determined by the system and utilized as a reference. Foreign substances having deviating characteristics are recognized if the sensed dimension along the smallest axis amounts to, for example, 5 mm. Such foreign substances may then be separated from the tuft stream A through a gate 29.

The housing 13 (also referred to as reflected light module) includes a semiconductor flash device 17 having a high homogeneity, a command-controlled, high-speed measuring camera 15 having a digital data output (for example, as disclosed in German offenlegungsschrift 43 13 621) and a deflecting mirror 19 for reducing the overall structural height. The housing 23 (also referred to as a transmitted light module) includes a large-area, semiconductor flash device 25 of high intensity. The additional housings 14 and 24 (also referred to as reflected light and, respectively, transmitted light modules) are constructed identically to the reflected light and transmitted light modules 13 and 23.

In operation, for the determination of foreign fiber, foreign substances, as well as lightness and/or color of the fiber material, expediently reflected light and transmitted light is utilized. Two pictures of the same object, one with transmitted light and one with reflected light are taken in a very rapid succession. Both images are combined and evaluated jointly. The light is applied as a flash and controlled by the camera 15 (and 16, if present) or by their control. For the individual pictures light of different wavelengths may be used in which case it is feasible to use a plurality of illuminating devices for any picture taking. For example, the reflected light module 13 may have more than one illuminating device which may operate at different wavelengths and wherein the illumination may occur from different directions or from different sides (transmitted light and reflected light). Also, the various directions, sides and wavelengths may be combined with one another and different flash durations may be set.

The camera 15, the illuminating devices 17, 25 as well as a power cylinder 30 operating a separating gate 29 are coupled to an electronic control and regulating device 31. The components of the modules 14 and 24, if present, are also connected to the electronic control and regulating device 31.

Figure 3:
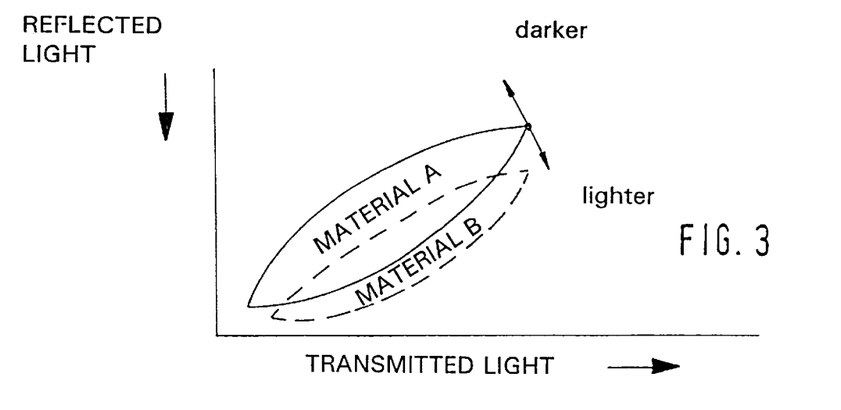
FIG. 3 is a diagram illustrating the use of reflected light as a function of the transmitted light for various fiber materials during the learning phase.

Between the camera 15 and the electronic control and regulating device 31 an electronic image processing device 32 is connected. Such a device may also be provided in a similar manner if the camera 16 is present. To the control and regulating device 31 there are further connected a monitor 33, a signal analyzing device 34, a memory 35, a comparator 36, a switching device 37 and a device 38 (see FIG. 3) for determining the location of each fiber bale 1' in the fiber bale series 1a, a machine control 39 (for example, for the mixer 4 and/or for the bale opener 1), a setting device 40 and a limit value forming device 46.

In operation, with the aid of the digital cameras 15 and 16, pictures based on reflected light and transmitted light of the fiber tufts are taken and the images are evaluated in a manner now to be described. It is assumed that the second set of modules 14, 24 is also present.

(1) During a learning phase, by taking, for example 500 exposures, the cameras 15 and 16 are trained for the material to be processed. During such a phase the separation of foreign substances is not optimized; coarse separation takes placed based on empirical data. The learning curve concerning the material may be seen in FIG. 3. The curve characterizing the material illustrates the region in which positively no separation should take place and is shifted dependent upon the lightness characteristics of the material and also changes its shape.

The material present in the mixture may be learned in different stages:

(a) As a mean value for all fiber bales 1' wherein the learning period may be one pass over all fiber bales 1';

(b) As a mean value for the bales 1' of one bale group, wherein the learning period may be, for example, one pass over a bale group;

(c) Individually for each fiber bale 1' of a bale series 1a or a bale group; for which purpose the X coordinate of the travel of the bale opener 1 is to be inputted in the control device 31 of the apparatus 11. Further, a synchronization with the motion start of the bale opener 1 should take place. For this purpose it is often expedient to move the bale opener 1 at a lower speed than during its usual operation;

(d) In one instance upon the new introduction of the bales 1';

(e) By a sliding mean value formation in several instances in steps, distributed over the removal height of the bales 1'; and (f) If required, values of previous, identical fiber bale series 1a may be utilized for forming the mean value or utilized for the purposes of a more rapid optimization.

Figure 4:
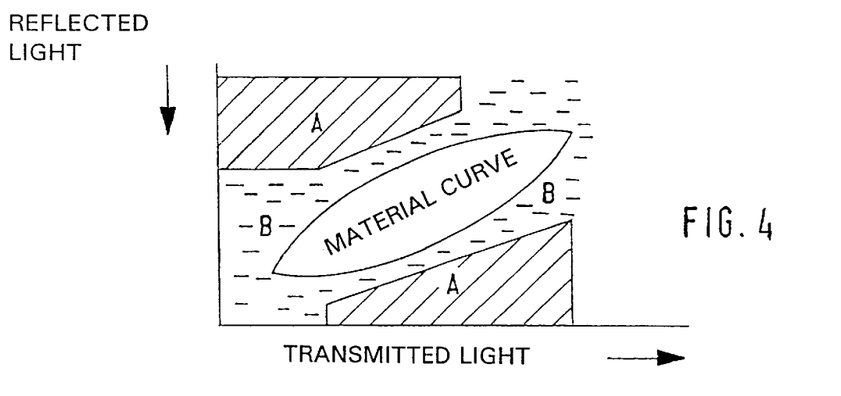
FIG. 4 is a diagram illustrating the function according to FIG. 3 with fixed separation sensitivity.

After forming the material-characteristic curve, the separation sensitivity for the separating device 29, 30 is set in two zones about the curve. With reference to FIG. 4, zone A represents the region of definite separation, effected immediately, while zone B represents a region of possible separation for which suitable testing algorithms are additionally utilized as concerns shape, lightness structure, lightness degree, etc.

Figure 5:
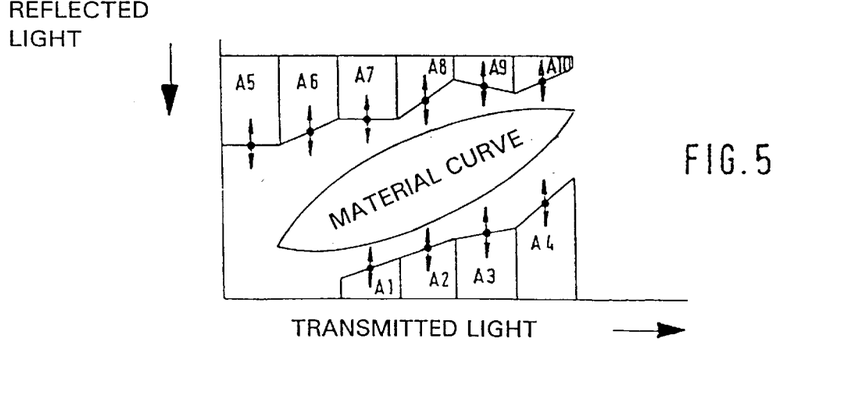
FIG. 5 is a diagram illustrating the function according to FIG. 4 with respect to various foreign substances.
Figure 6A:
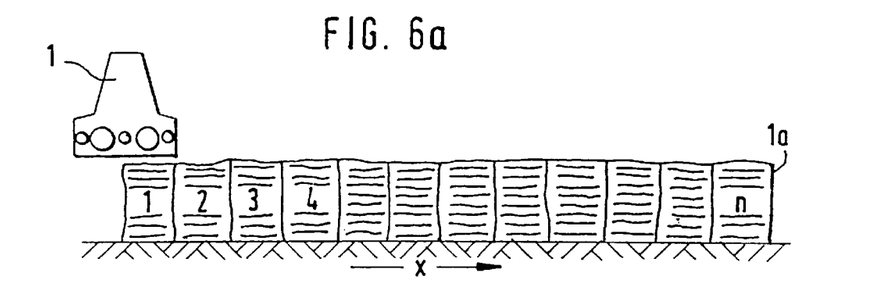
FIG. 6a is a schematic side elevational view of a row of fiber bales and a fiber bale opener disposed thereabove.
Figure 6B:
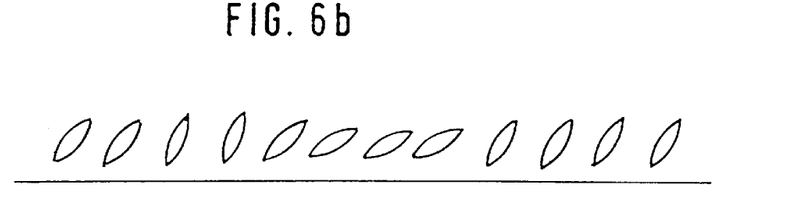
Figure 6C:
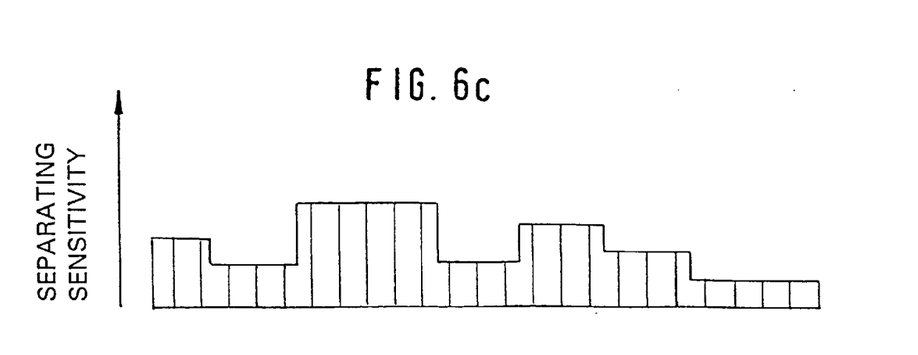

The setting of the separating sensitivity in the zone A may be effected (a) within defined boundaries for all materials;

(b) at a fixed distance to the material curve of the respective material (according to the possibilities 1a, 2f discussed above), wherein the zone A is adapted to the respective material curve as shown in FIG. 4;

(c) with a variable distance according to classes which are typical for foreign particles as shown in FIG. 5;

(d) additionally, by an automatic and/or semi-automatic variation of the boundaries in predetermined time intervals according to the separation frequency (excessively little or too much separation);

according to a comparison with the separation of other bale types or earlier bale series; and according to the appearing problems in the subsequent process, for example, an increase of the cutting frequencies of the foreign fiber yarn cleaner at spool machines or open end spinning machines.

(2) The separations are to be plotted according to the type of the impurity (for example, jute or foil) and the frequency of occurrence and may be evaluated:

(a) for a selectable period (for example, layer)

(b) for one or more fiber bale series 1a or bale groups;

(c) for determined bale types or individual bales 1' for detecting particularly contaminated bales.

(3) The shift of the material curves in a fiber bale series 1a may also be utilized over the fiber tuft removal period or between various fiber bale series 1a as a measure for the lightness differences in the mixture for the following purposes:

(a) to detect impermissible deviations in the lightness or color of the material (danger of streaks in the fabrics);

(b) to detect and if needed, to separate individual, excessively light or excessively dark bales 1' (for example, to find erroneously located bales 1');

(c) to use these values for the intended control of the after-connected mixer 4 (for example, chute switching in the mixer);

(d) to make predictions concerning the lightness of the yarn to be processed; and (e) in the continuously operating bale opener (which may be a BDT 020 model manufactured by Trützschler GmbH & Co. KG, Mönchengladbach, Germany) to automatically control the bale series 1a with respect to lightness fluctuations.

For a reliable operation of the apparatus 11, the cameras 15 and 16 must be situated at a sufficient distance upstream of the separating device 29, 30 as viewed in the direction of fiber travel. Should this not be the case, there are risks that the foreign substances already have passed the separating device before the separating gate 29 is pivoted into its separating position. Tests have shown that the period elapsing from the detection of a foreign substance until the gate 29 has moved to provide access to the waste conduit 47 amounts to 0.2 sec. Thus, in case of a velocity of 10 m/s of the fiber/air mixture in the pneumatic conveying conduit, the distance of the cameras 15 and 16 from the gate 29 should be greater than 2 m. Considering an appropriate safety factor such a distance should preferably be 3 m. Since, particularly larger fiber tufts travel through the conduit 9 with a lesser speed than that of the fiber/air mixture, the separating (waste) conduit 47 must also not be closed prematurely. Otherwise there are risks that the foreign substance arrives at the gate 29 at a time when the waste conduit 47 is already closed and thus the foreign substance is further conveyed into the conduit portion 9b. Tests have shown that in case of a fiber/air velocity of 10 m/sec in the conveying conduit 9 and a distance of 3 m between the cameras 15, 16 and the gate 29, an open period of 1 sec for the waste conduit 47 suffices to securely separate all foreign substances. This period may be set in the control part of the cameras 15 and 16 and may be changed for different delivery speeds in conduit 9.

Two exposures are made of the same object in a rapid sequence. From the distance of the detected object in the picture and from the delay between the two exposures the velocity of the object, that is, the foreign substance itself or together with the fiber tuft may be determined. From the velocity the time is computed which is required for the object to reach the separating gate 29. The thus-determined period is applied to the control device 31 and is utilized for opening the gate 29 to separate the detected object. In this manner reduction of the separated quantities (particularly good fibers) is made possible because the time slot during which the gate 29 remains open may be smaller. Otherwise, since the objects have different velocities in the fiber tuft stream, such a large time window would have to be set that both the fastest and the slowest substances may be separated.

First, the determination of the conveying speed $v_1$ of the foreign substance in the zone of the cameras 15 and 16 is determined:

$$v_1 = \frac{d}{t_1}$$

wherein $v_1$=the conveying speed of the detected object d=the distance between two pictures $t_1$=conveying period for the distance d.

Thereafter, the transport period $t_2$ of the object from the cameras 15, 16 to the separating gate 29 is determined:

$$t_2 = \frac{e}{v_1},$$

wherein $t_2$=conveying period through the distance e e=the distance between the second picture and the separating gate 29

$v_1$=the conveying speed of the detected object.

The period $t_2$ computed in the above manner is utilized for energizing and de-energizing the pneumatic cylinder 30 for operating the separating gate 29.

The location of each fiber bale 1' within the fiber bale series 1a may be determined, for example, by means of an apparatus disclosed in German Offenlegungsschrift (application published without examination) 41 19 888.

Figure 7:
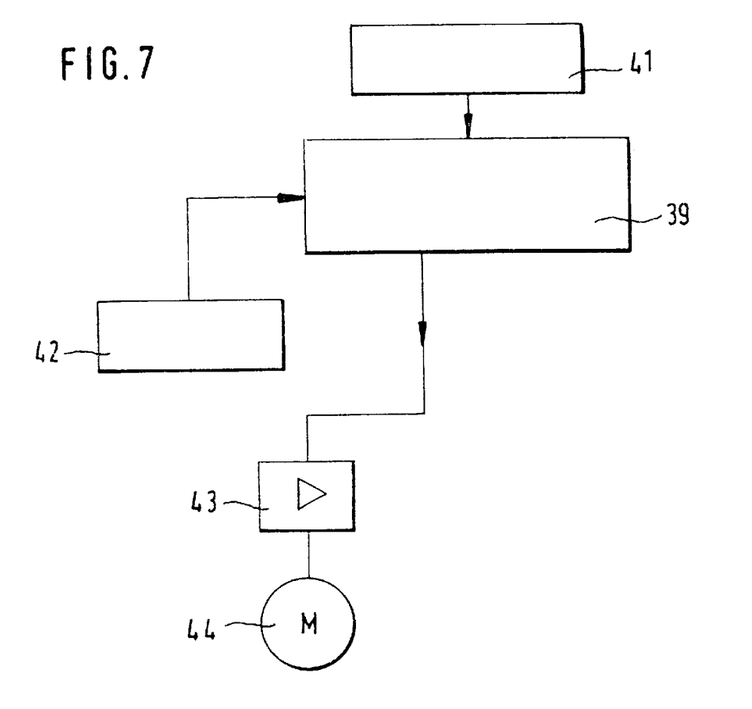
FIG. 7 is a block diagram including a control device, an X-axis path sensor and a drive motor for the bale opener.

In FIG. 7 a control device 39 (for example, a memory-programmable control) is shown to which an inputting device 41 is connected. A path detector 42, for example, an incremental path sensor mounted on the carriage of the travelling bale opener 1 is electrically connected with the control device 39 for determining the X axis of travel of the bale opener 1. Further, the control device 39 is connected, via an amplifier 43 (control electronics, frequency converter) with the propelling motor 44 for the carriage of the bale opener 1 travelling along the X axis.

The width of each fiber bale 1' and its sequence within a bale series 1a may be determined, for example, with a method and an apparatus disclosed in German Offenlegungsschrift 43 20 403.

Figure 8:
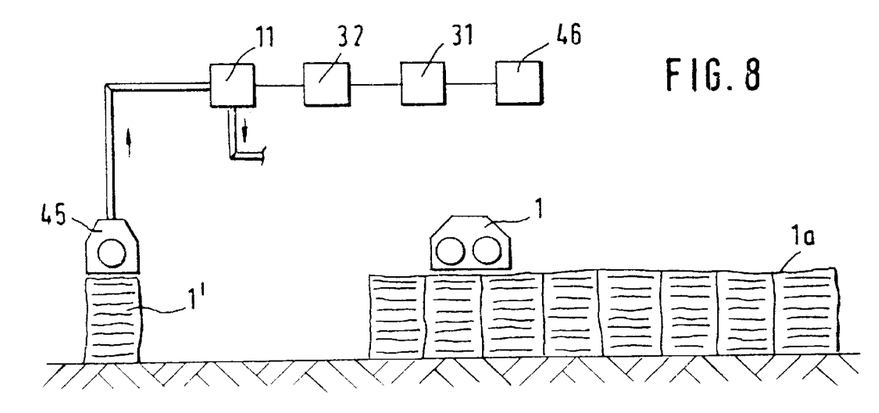
FIG. 8 is a schematic side elevational view, with block diagram, illustrating a bale testing apparatus according to the invention, situated ahead of the fiber bale series to be opened.

In the FIG. 8 arrangement the apparatus 11 according to the invention is used for examining a fiber bale 1' which is situated ahead of a fiber bale series 1a to be opened. The arrangement includes a bale opening device 45 which is composed, for example, of a rapidly rotating toothed device (roll) similar to the bale opener 1 and the optical sensor apparatus 11 including an image processing device 32 as well as a control and regulating device 31 and an zutput device 46.

It will be understood that the above description of the present invention is susceptible to various modifications, changes and adaptations, and the same are intended to be comprehended within the meaning and range of equivalents of the appended claims.

What is claimed is:

1. A method of processing fiber comprising the following steps:

(a) removing fiber tufts from a series of fiber bales;

(b) pneumatically conveying the fiber tufts in a duct;

(c) forming images of the conveyed material as it passes through a first location of the duct;

(d) determining at least one of a degree of lightness and a color of the fiber tufts by an image processing device;

(e) determining a degree of lightness of foreign substances, conveyed with the fiber tufts, by the image processing device;

(f) comparing the measuring values obtained by the image processing device in steps (d) and (e) with at least one settable limit value;

(g) initiating a switching operation when said limit value is exceeded for branching off the fiber tufts to a waste receiver from the duct at a second location thereof; said second location being situated downstream of said first location as viewed in a conveying direction of the fiber tufts; and (h) establishing a sensitivity of performing step (g) within defined limit values for all types of fiber material.

2. The method as defined in claim 1, further comprising the step of operating a display when said limit value is exceeded.

3. The method as defined in claim 1, further comprising the step of performing a test run for determining lightness characteristics of the fiber tufts.

4. The method as defined in claim 3, further comprising the step of determining said limit value based on said lightness characteristics.

5. The method as defined in claim 3, further comprising the step of forming a mean lightness value.

6. The method as defined in claim 5, further comprising the step of forming a mean lightness value for all bales of the fiber bale series.

7. The method as defined in claim 5, further comprising the step of forming a mean lightness value for a fiber bale group forming a part of the fiber bale series and being characterized by a common fiber property.

8. The method as defined in claim 1, wherein the sensitivity of performing step (g) is established at a distance relative to the lightness characteristics for a determined fiber material.

9. The method as defined in claim 1, wherein the sensitivity of performing step (g) is established at a variable distance relative to the lightness characteristics of a fiber material as a function of typical properties of foreign substances conveyed with the fiber tufts.

10. The method as defined in claim 1, further comprising the step of determining the location of each fiber bale within the bale series and associating one of the lightness and degree of contamination of the fiber material with the particular fiber bales on which step (a) was performed.

11. The method as defined in claim 1, further comprising the step of associating with each fiber bale a limit value for performing step (g).

12. The method as defined in claim 11, further comprising the step of determining the limit values for each fiber bale on the basis of measuring values obtained in the image processing device.

13. An apparatus for recognizing foreign substances in and separating the foreign substances from a material stream including fiber tufts, previously removed from fiber bales, commingled with the foreign substances, comprising (a) a duct in which the material stream travels;

(b) an electronic control and regulating device;

(c) an optical sensor device for forming images of the material stream at a first location of the duct;

(d) an image processing device being connected to said electronic control and regulating device and said optical sensor device;

(e) a separating device disposed at a second location of said duct for selectively deviating the material stream from said duct into a waste receiver; said separating device being connected to said electronic control and regulating device for actuating said separating device as a function of signals emitted by said image processing devices; and (f) means for setting a sensitivity of said separating device.

14. The apparatus as defined in claim 13, further comprising a signal analyzing device connected to said electronic control and regulating device for processing measuring signals emitted by said image processing device.

15. The apparatus as defined in claim 13, further comprising a memory for receiving measuring signals generated during test runs; said memory being connected to said electronic control and regulating device.

16. The apparatus as defined in claim 13, further comprising a limit value forming device connected to said electronic control and regulating device.

17. The apparatus as defined in claim 13, further comprising a display device connected to said electronic control and regulating device.

18. The apparatus as defined in claim 13, further comprising a machine control device connected to said electronic control and regulating device.

* * * * *